(12) United States Patent
Zhang et al.

(10) Patent No.: US 7,579,016 B2
(45) Date of Patent: *Aug. 25, 2009

(54) METHODS FOR REPELLING ARTHROPODS USING ISOLONGIFOLENONE ANALOGS

(75) Inventors: Aijun Zhang, Silver Spring, MD (US); John F. Carroll, Beltsville, MD (US); Shifa Wang, Nanjing (CN); Jerome A. Klun, Potomac, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/106,505

(22) Filed: Apr. 21, 2008

(65) Prior Publication Data

US 2009/0018192 A1    Jan. 15, 2009

Related U.S. Application Data

(63) Continuation-in-part of application No. 11/777,795, filed on Jul. 13, 2007, now Pat. No. 7,378,557.

(51) Int. Cl.
*A01N 25/34* (2006.01)
*A61K 31/12* (2006.01)

(52) U.S. Cl. .................................. 424/403; 514/690
(58) Field of Classification Search ................. 514/690; 424/403
See application file for complete search history.

(56) References Cited

U.S. PATENT DOCUMENTS

| | | | | |
|---|---|---|---|---|
| 3,647,847 | A * | 3/1972 | Curtis et al. ................. | 560/249 |
| 3,718,698 | A | 2/1973 | Hall | |
| 5,030,739 | A * | 7/1991 | Foricher et al. ............. | 552/542 |
| 6,734,159 | B2 * | 5/2004 | Pickenhagen et al. ......... | 512/19 |
| 7,378,557 | B1 * | 5/2008 | Zhang et al. ................. | 568/342 |

FOREIGN PATENT DOCUMENTS

| | | |
|---|---|---|
| GB | 1256535 | 9/1968 |
| GB | 1505821 | 1/1974 |
| NL | 10038544 | 2/2002 |

OTHER PUBLICATIONS

Zhang, A., "Isolongiotenone: A Novel Sesquiterpene Repellent of Ticks and Mosquitoes", Journal of Medical Entomology, vol. 46, (1), pp. 100-106, Jan. 2009.
Wang, S., et al., "Facile and Efficient Synthesis of Isolongifolenone", OPPI Briefs, vol. 40, (4), pp. 405-410, 2008.
Klun, J., et al., "A Quantitative in Vitro Assay for Chemical Mosquito-Deterrent Activity Without Human Blood Cells", Journal of the American Mosquito Control Association, vol. 24, (4), pp. 508-512, 2008.
De bruyn, M., et al., "Chemoselective Reduction of Complex α,β-Unsaturated Ketones to Allylic Alcohols over Ir-Metal Particles on β-Zeolites", Angew. Chem. Int. Ed., 2003, (42), pp. 5333-5336.
Pearson, A., et al., "Oxidation of Alkenes to Enones Using tert-Butyl Hydroperoxide in the Presence of Chromium Carbonyl Catalysts", Tetrahedron Letters, vol. 25, No. 12, pp. 1235-1238, 1984.
Ranganathan, R., et al., "Studies in Sesquiterpenes-XL", Tetrahedron, vol. 26, pp. 621-630, 1970.
Shieh, B., et al., "Synthesis of Optically Active 9-Oxoisolongifolene", Department of Applied Chemistry, Studies on the Oxidation of Terpenes in Polar Aprotic Solvents, (6), 1978.
Prahlad, J.R., et al., "On the Structure of Isolongifolene", Tetrahedron Letters, (8), pp. 417-427, 1964.
Lala, L.K., et al., "Products of the Action of Peracetic Acid on Isolongifolene", Journal of Organic Chemistry, vol. 35,(4), pp. 1172-1173, Apr. 1970.
Mihelich, E., et al., "One-Pot Conversion of Olefins to α,β-UnsaturatedCarbonyl Compounds. An Easy Synthesis of 2-Cyclopentenone and Related Compounds", Journal of Organic Chemistry, vol. 48, pp. 4135-4137, 1983.
Pearson, A., et al., "A New Method for the Oxidation of Alkenes to Enones. An Efficient Synthesis of Δ5-7- Oxo Steroids", Chem. Soc. Perkin Trans., I, pp. 267-273, 1985.
Journal of Chemical Research, Issue 3, Miniprint, pp. 746-754, 1977.
Dauben, W., et al., "Allylic Oxidation of Olefins with Chromium Trioxide-Pyridine Complex", Allylic Oxidation of Olefins, vol. 34, (11), pp. 3587-3592, Nov. 1969.
Muthyala, R., et al., "Bridged Bicyclic Cores Containing a 1,1-Diarylethylene Motif Are High-Affinity Subtype-Selective Ligands for the Estrogen Receptor", J. Med. Chem., vol. 46, pp. 1589-1602, 2003.
Shiino, M., et al., "Synthesis of N-substituted N-nitrosohydroxylamines as Inhibitors of Mushroom Tyrosinase", Bioorganic and Medicinal Chemistry, vol. 9, pp. 1233-1240, 2001.
Choudhary, M. I., et al., "Microbial Transformation of Isolongifolen-4-one", Helvetica Chemica Acta, vol. 86, pp. 3450-3460, 2003.
Da Silva, T.B.C., et al., "Chemical Constituents and Preliminary Antimalarial Acivity of *Humiria balsamifera*", Pharmaceutical Biology, vol. 42, (2), pp. 94-97, 2004.
Liu, Z., Chemistry and Industry of Forest Products, vol. 17, (2), Jun. 1997.
Fa-Wen, W., et al., "The Application of Oxygen-enriched Air by Gas Separation Membranes in Catalytic Oxidation of Isolongifolene", Journal of Nanjing University (Natural Sciences), vol. 42, (2), Mar. 2006.
Giovanelli, E., et al., "Straightforward Conversion of Alcohols into Dibenzenesulfonimides", Science Direct, Tetrahedron Leters 47, pp. 8457-8458, 2006.
McCabe, E.T., et al., "Insect Repellents. III. N, N-Diethylamides", Bureau of Entomology and Plant Quarantine, Agricultural Research Administration, U.S. Department of Agriculture, pp. 493-498, Received Oct. 30, 1953.

(Continued)

*Primary Examiner*—Sikarl A Witherspoon
(74) *Attorney, Agent, or Firm*—John D. Fado; G. Byron Stover

(57) ABSTRACT

A method for for repelling arthropods involving treating an object or area with an arthropod repelling effective amount of at least one isolongifolenone analog (and optionally a carrier or carrier material).

26 Claims, 7 Drawing Sheets

OTHER PUBLICATIONS

Novak, R., et al., "Natural-Based Repellent Products: Efficacy for Military and General Public Uses", Journal of the American Mosquito Control Association, vol. 21, (4) Supplement 7-11, 2005.

Carroll, J.F., et al., "Repellency of Deet and SS220 Applied to Skin Involves Olfactory Sensing by Two Species of Ticks", Medical and Veterinary Entomology, vol. 19, pp. 101-106, 2005.

Dethier, V.G., et al., "The Designation of Chemicals in Terms of the Responses They Elicit from Insects", Journal of Economic Entomology, vol. 53, (1), pp. 134-136, Feb. 1960.

Taubes, G., "A Mosquito Bites Back", The New York Times, pp. 40-46, Aug. 24, 1997, Retrieved from NYTimes.Com Jan. 25, 2007.

Xue, R.D., et al., "Laboratory and Field Evaluation of Insect Repellents as Oviposition Deterrents Against the Mosquito *Aedes albopictus*", Medical and Veterinary Entomology, vol. 15, pp. 126-131, 2001.

DeBiasi, R., et al., "West Nile Virus Meningoencephalitis", Nat Clin Pract Neurol., vol. 2, (5), pp. 264-275, 2006, retrieved from Medscape Mar. 12, 2007.

Klun, J., et al., "A New In Vitro Bioassay System For Discovery of Novel Human-Use Mosquito Repellents", Journal of the American Mosquito Control Association, vol. 21, (1), pp. 64-70, 2005.

Klun, J., et al., "A New Module for Quantitative Evaluation of Repellent Efficacy Using Human Subjects", Journal of Medical Entomology, vol. 37, (1), pp. 177-181, 2000.

Chemicalland21.com, tert-Butyl Hydroperoxide, pp. 1-2, Retrieved Feb. 10, 2009.

Budavari, S., et al., "The Merck Index", Eleventh Edition, Merck & Co. Publishing, p. 2240, 1989.

\* cited by examiner

J4-118
(−)-Isolongifolenone

J4-120A

J4-120B

J4-120C

J4-120D

J4-120E

J4-120F
(−)-Isolongifolanone

METHODS FOR REPELLING ARTHROPODS USING ISOLONGIFOLENONE ANALOGS

REFERENCE TO RELATED APPLICATION

This application claims the benefit of U.S. patent application Ser. No. 11/777,795, filed 13 Jul. 2007, which is incorporated herein by reference in its entirety.

BACKGROUND OF THE INVENTION

The present invention relates to the use of isolongifolenone analogs to repel arthropods by treating an object or area with an arthropod repelling effective amount of at least one isolongifolenone analog (and optionally a carrier or carrier material).

Diseases transmitted by blood-feeding arthropods are a serious threat to public health worldwide. More than 700 million cases of mosquito transmitted disease were reported annually (Shell, E. R., Atlantic Monthly, pp. 45-60, August 1997:. Over three billion people live under the threat of malaria, which kills over a million people each year (WHO World Malaria Report 2005, Roll Back Malaria, World Health Organization, UNICEF, http://rbm.who.int/wmr2005). In the United States, West Nile virus was transmitted by mosquitoes to more than 8,000 people from 1999-2005, resulting in over 780 deaths (DeBiasi, R. L., and K. L. Tyler, Nat. Clin. Pract. Neurol., 2:264-275 (2006)). N,N-Diethyltoluamide (Deet) is considered to be the best insect repellent ever developed and is the most widely used insect repellent worldwide with tens of millions of dollars in annual sales (Osimitz, T. G., and R. H. Grothaus, J. Am. Mosq. Control. Assoc., 11: 274-278 (1995)). However, Deet dissolves plastics and paints and clinical literature reports the association of Deet with neurotoxicity in humans (Robbins, P. J., and M. G. Cherniack, J. Toxicol. Environ. Health, 18: 503-525 (1986)). Thus, there is a great need for effective alternatives to Deet.

We previously found that (−)-isolongifolenone, which occurs in nature in trace amounts, is more effective than Deet in repelling ticks and deterring feeding mosquitoes. With high repellent efficiency, this compound will allow much wider application by the public and the military. We have also found that some isolongifolenone analogs have repellent and deterrent activities comparable to isolongifolenone. Therefore, isolongifolenone- and some isolongifolenone analogs have a great potential to displace Deet in the worldwide repellent market.

SUMMARY OF THE INVENTION

In accordance with the present invention there is provided a method for repelling -arthropods involving treating an object or area with an arthropod repelling effective amount of at least one isolongifolenone analog (and optionally a carrier or carrier material). Generally the isolongifolenone analogs have the following formula:

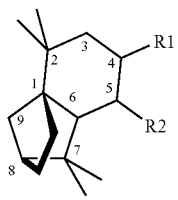

wherein $R_1$ is hydrogen, an oxygen, a $C_{1-10}$ alcohol (straight or branched), aldehyde, alkyl, ether (e.g. methanol, ethanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid) and $R_2$ is hydrogen, an oxygen, a $C_{1-10}$ alcohol (straight or branched), aldehyde, alkyl, ether (e.g. methanol, ethanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid); optionally there is a double bond between carbons 5 and 6 and $R_2$ is hydrogen. Preferably $R_1$ or $R_2$ are hydrogen (in other words, $R_1$ can be hydrogen or $R_2$ can be hydrogen or both $R_1$ and $R_2$ can be hydrogen). Preferably $R_1$ and $R_2$ are not both hydrogen (in other words if $R_1$ is hydrogen then $R_2$ is not hydrogen or if $R_2$ is hydrogen then $R_1$ is not hydrogen).

Also, in accordance with the present invention is a composition containing at least one isolongifolenone analog (1S, 8S)-2,2,7,7-tetramethyltricyclo[6.2.1.0$^{1,6}$]undecane having the, following formula:

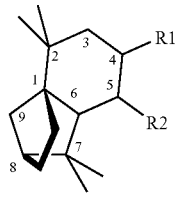

wherein $R_1$ is hydrogen, an oxygen, a $C_{1-10}$ alcohol (straight or branched), aldehyde, alkyl, ether (e.g. methanol, ethanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid) and $R_2$ is hydrogen, an oxygen, a $C_{1-10}$ alcohol (straight or branched), aldehyde, alkyl, ether (e.g. methanol, ethanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid); optionally there is a double bond between carbons 5 and 6 and $R_2$ is hydrogen. Preferably $R_1$ or $R_2$ are hydrogen (in other words, $R_1$ can be hydrogen or $R_2$ can be hydrogen or both $R_1$ and $R_2$ can be hydrogen). Preferably $R_1$ and $R_2$ are not both hydrogen (in other words if $R_1$ is hydrogen then $R_2$ is not hydrogen or if $R_2$ is hydrogen then $R_1$ is not hydrogen); and optionally a carrier or carrier material.

Further in accordance with the present invention is a composition containing at least one (1R,8S)-2,2,7,7-tetramethyltricyclo[6.2.1.0$^{1,6}$]undec-5-ene having the formula:

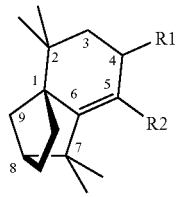

wherein $R_1$ is hydrogen, an oxygen, a $C_{1-10}$ alcohol (straight or branched), aldehyde, alkyl, ether (e.g. methanol, ethanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid) and $R_2$ is hydrogen; and optionally a carrier or carrier material.

Also, in accordance with the present invention is a composition containing at least one (1S,8S)-2,2,7,7-tetramethyltricyclo[6.2.1.0$^{1,6}$]undecane having the formula:

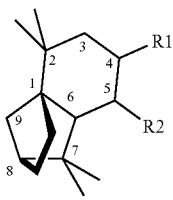

wherein $R_1$ is hydrogen, an oxygen, a $C_{1-10}$ alcohol (straight or branched), aldehyde, alkyl, ether (e.g. methanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid) and $R_2$ is hydrogen; and optionally a carrier or carrier material.

Further in accordance with the present invention is a composition containing at least one tricyclo(1S,8S)-2,2,7,7-tetramethyltricyclo[6.2.1.0$^{1,6}$]undecane having the formula:

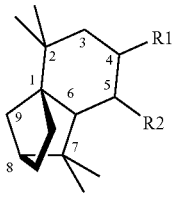

wherein $R_2$ is an oxygen, a $C_{1-10}$ alcohol (straight or branched), aldehyde, alkyl, ether (e.g. methanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid) and $R_1$ is hydrogen; and optionally a carrier or carrier material.

DETAILED DESCRIPTION OF THE INVENTION

Figure 1:
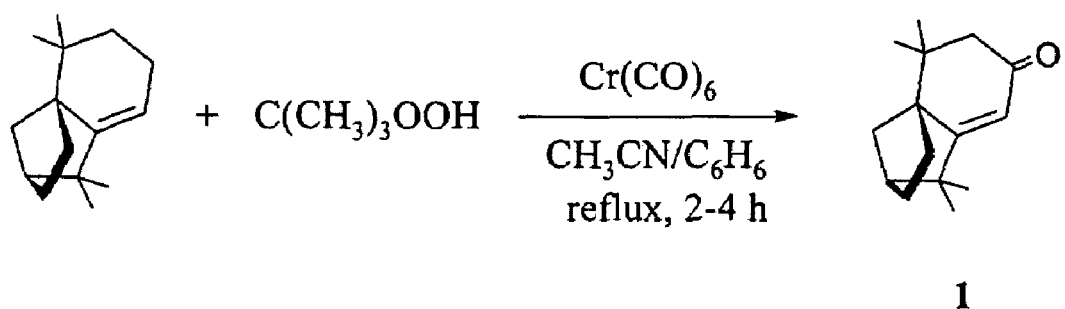
FIG. 1 shows preparation of isolongifolenone 1 from isolongifolene.

We have successfully converted isolongifolene into isolongifolenone 1 (FIG. 1) utilizing tert-butyl hydroperoxide as the oxidant and chromium hexacarbonyl as the catalyst (which can be recycled). This method uses a short reaction time and results in a high purity, high yield product. For example, the conversion rate was about 99% (e.g., 99%) and about 90% (e.g., 90%) isolongifolenone was formed after about 2 h (e.g., 2 h) oxidation; at about 3.5 h (e.g., 3.5 h), the isolongifolene was oxidized to about 100% (e.g., 100%) and about 93% (e.g., 93%) yield isolongifolenone was achieved. Chemical purity of crude product was about 94% (e.g., 94%). After flash column chromatography purification, chemical purity can be > about 99% (e.g., >99%).

Generally, isolongifolenone is produced by reacting a solution containing (−)-isolongifolene, chromium hexacarbonyl, and t-butyl hydroperoxide; the solution generally also contains acetonitrile and benzene. Generally, the solution contains about 1 (e.g., 1) molar isolongifolenone, about 0.3-about 1 (e.g., 0.3-1) molar equivalents of chromium hexacarbonyl, about 2-about 5 (e.g., 2-5) molar equivalents of 1-butyl hydroperoxide, and about 80-about 95% (e.g., 80-95%) (w/w) acetonitrile, and about 8-about 9.5% (e.g., 8-9.5%) (w/w) benzene based on isolongifolenone. The solution is heated (generally about 80° to about 82° C. (e.g., 80°-82° C.)) for about 2 to about 4 hours (e.g., 2-4 hours). The solution is then cooled to room temperature (e.g., using an ice-bath), filtered, and the precipitate (chromium hexacarbonyl) is washed with cold benzene. The filtrate is diluted with hexane and washed with water, brine, and dried over $Na_2SO_4$. The solvent is evaporated under reduced pressure to give crude product (about 94% (e.g., 94%) purity). The isolongifolenone may be purified (e.g., by a flash chromatography on silica gel 60 Å (Fisher, 230-400 mesh) using hexane-ethyl acetate as eluent) to provide isolongifolenone 1 as a white semi-solid at room temperature (> about 99% (e.g., >99%) purity). The starting material, isolongifolene, for production of isolongifolenone is also commercially available as a feed stock in kg to ton quantities (Zizhu Pharmaceutical Co., 2008, (http://www.buyersguidechem.de/AliefAus.php?pname=Isolongifolene&pnu=40802573875&cass=).

To recycle the catalyst, the liquid phase is withdrawn by glass pipette from the reaction flask when the reaction is finished, and the precipitate is washed several times with cold benzene; and then 15% less amount of isolongifolene (liquid phase may dissolve a little catalyst) and oxidant can be used for subsequent oxidation.

Isolongifolenone is known to have importance in industry because its derivatives are widely used in fragrances, perfumes, space sprays, cosmetics, detergents, deodorants, fabrics, fibers, and paper products (GB Patent No. 1,256,535; U.S. Pat. No. 3,647,847; GB Patent No. 1505821; U.S. Pat. No. 3,718,698; DE Patent No. 10,038,544 A1; U.S. Pat. No. 6,734,159; De Bruyn, M., et al., Angew. Chem. Internat. Edit., 42: 5333-5336 (2003)). In addition, isolongifolenone and other derivatives have been discovered to be active against tyrosinase, which is a multifunctional copper-containing enzyme for melanin biosynthesis in plants and animals (Choudhary, M. I., et al., Helv. Chim. Ada, 86: 3450-3460 (2003)). Recently, crude extracts from the stems and leaves of *Humiria balsamifera* St. (Aubl.) Hill (Humiriaceae), which is distributed commonly in the Amazon and northeast regions of Brazil, have been found to possess antimalarial activity (Da Silva, T. B. C., et al., Pharm. Biol., 42: 94-97 (2004)). Several compounds, including isolongifolenone, have been isolated and identified as the natural products in these plant species.

We have also found that isolongifolenone and some isolongifolenone analogs can be used to repel arthropods. Thus, the present invention also relates to a method for repelling arthropods involving treating an object or area with an arthropod repelling effective amount of isolongifolenone or at least one isolongifolenone analog, and optionally a carrier or carrier material known in the art. The method of the present invention may utilize a composition containing isolongifolenone or at least one isolongifolenone analog, and optionally a carrier or carrier material. The carrier or carrier material may be, for example, agronomically or physiologically or pharmaceutically acceptable carriers or carrier material.

Generally the isolongifolenone analogs have the following formula:

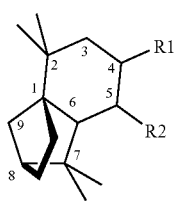

wherein $R_1$ is hydrogen, an oxygen, a $C_{1-10}$ alcohol (straight or branched), aldehyde, alkyl, ether (e.g. methanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid) and $R_2$ is hydrogen, an oxygen, a $C_{1-10}$ alcohol (straight or branched), aldehyde, alkyl, ether (e.g. methanol, ethanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid); optionally there is a double bond between carbons 5 and 6 and $R_2$ is hydrogen. Preferably $R_1$ or $R_2$ are hydrogen (in other words, $R_1$ can be hydrogen or $R_2$ can be hydrogen or both $R_1$ and $R_2$ can be hydrogen). Preferably $R_1$ and $R_2$ are not both hydrogen (in other words if $R_1$ is hydrogen then $R_2$ is not hydrogen or if $R_2$ is hydrogen then $R_1$ is not hydrogen).

The isolongifolenone analogs can be a (1R,8S)-2,2,7,7-tetramethyltricyclo[6.2.1.0$^{1,6}$]undec-5-ene having the formula:

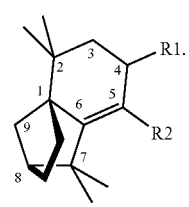

wherein $R_1$ is hydrogen, an oxygen, a $C_{1-10}$ alcohol (straight or branched), aldehyde, alkyl, ether (e.g. methanol, ethanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid) and $R_2$ is hydrogen.

The isolongifolenone analogs can be a (1S,8S)-2,2,7,7-tetramethyltricyclo[6.2.1.0$^{1,6}$]undecane having the formula:

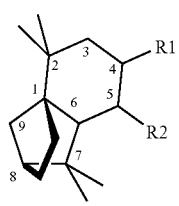

wherein $R_1$ is hydrogen, an oxygen, a $C_{1-10}$ alcohol (straight or branched), aldehyde, alkyl, ether (e.g. methanol, ethanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid) and $R_2$ is hydrogen; and optionally a carrier or carrier material.

The isolongifolenone analogs can be a tricyclo(1S,8S)-2,2,7,7-tetramethyltricyclo[6.2.1.0$^{1,6}$]undecane having the formula:

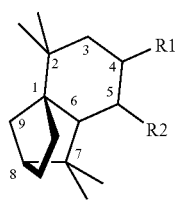

wherein $R_2$ is an oxygen, a $C_{1-10}$ alcohol (straight or branched), aldehyde, alkyl, ether (e.g. methanol, ethanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid) and R₁ is hydrogen; and optionally a carrier or carrier material.

The isolongifolenone analogs can be a (1S,8S)-2,2,7,7-tetramethyltricyclo[6.2.1.0¹,⁶]undecane having the formula:

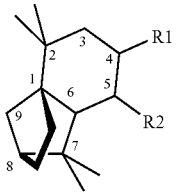

wherein $R^1$ is an oxygen, a $C_{1-10}$ alcohol (straight or branched), aldehyde, alkyl, ether (e.g. methanol, ethanal, 4-methylhexane, heptyloxymethane), or esters of said with a $C_{1-10}$ saturated or unsaturated, straight or branched acid (e.g., formic acid, acetic acid, 2-methylbutyric acid, 3-methyl-2-butenoic acid) and $R^2$ is an oxygen, a $C_{1-10}$ alcohol (straight or branched), aldehyde, alkyl, ether (e.g. methanol, ethanal, 4-methylhexane, heptyloxymethane), or esters of said alcohol with a $C_{1-10}$ saturated or unsaturated, straight or branched acid (e.g., formic acid, acetic acid, 2-methylbutyric acid, 3-methyl-2-butenoic acid); and optionally a carrier or carrier material.

Figure 5:
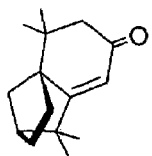
FIG. 5 shows the structures of (−)-isolongifolenone (J4-118) and some analogs of isolongifolenone.
Figure 5:
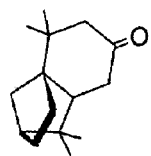
Figure 5:
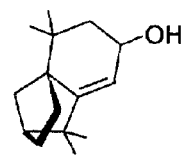
Figure 5:
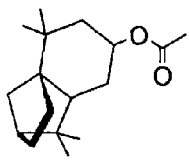
Figure 5:
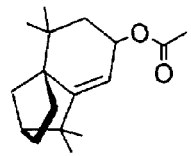
Figure 5:
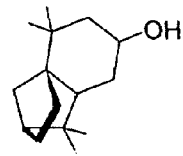
Figure 5:
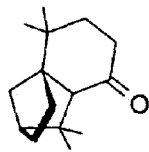

Preferably the isolongifolenone analogs are one of the compounds in FIG. 5 (excluding isolongifolenone).

The optical isomers of isolongifolenone analogs could be (+)- or (−)-; depending on the starting material isolongifolene or longifolene.

The isolongifolenone analogs were synthesized according to known methods:Synthesis of dihydroisolongifolenone (J4-120A) (Prahlad, J. R.,et al., Tetrahedron Lett., 5: 417-427 (1964); Ranganathan, R., et al., Tetrahedron, 26: 621-630 (1970)). Synthesis of isolongifolenyl alcohol (J4-120B) (Curtis, A. J., et al., GB Patent No. 1,256,535 (1971); Banthorpe, D. V., Tetrahedron Lett., 36: 3865-3868 (1972); Pickenhagen, W., and D. Schatkowski, U.S. Pat. No. 6,734,159 B2 (2004)). Synthesis of dihydroisolongifolenyl alcohol (J4-120E), same procedure as J4-120B. Synthesis of dihydroisolongifolenyl alcohol acetate (J4-120C) (Raucher, S., et al., J. Am. Chem. Soc., 103: 1853-1855 (1981); Pinheiro, S., et al., Tetrahedron Asymmetry, 11:3495-3502 (2000)). Synthesis of isolongifolenyl alcohol acetate (J4-120D), same procedure as J4-120C. Synthesis of isolongifolenone (J4-120F) (U.S. Pat. No. 5,426,095); it was obtained from Bedoukian Research Inc. as a gift.

An arthropod repellent is any compound or composition which deters insects from biting and feeding on a host. Thus, the term "repelling" is defined as inhibiting feeding by arthropods when a chemical is present in a place where insects (e.g., *Aedes aegypti*) would, in the absence of the-chemical, feed, and it also includes causing arthropods (e.g., flies and ticks) to make oriented movements away from a source of a chemical repellent (Dethier, V. L., et al., J. Econ. Ent., 53: 134-136 (1960)). Thus, the term "repelling" also includes reducing the number of arthropod (e.g., *Aedes aegypti*) bites on a treated area or object (e.g., mammalian skin which has been treated topically with the compositions or compounds of the present invention) when compared to the same area or object which is untreated, and the term "repelling" also includes causing arthropods (e.g., ticks) to make oriented movements away from a treated area or object (e.g., mammalian skin which has been treated topically with the compositions or compounds of the present invention) when compared to the same area or object which is untreated.

The method for repelling arthropods from an object (e.g., mammals such as humans) or area (e.g., a surface such as human skin) involves treating (or exposing) the object or area with isolongifolenone or at least one isolongifolenone analog, and optionally including a carrier material or carrier. The terms "object" or "area" as used herein include any place where the presence of target pests is not desirable, including any type of premises, which can be out-of-doors, such as in gardens, lawns, tents, camping bed nets, camping areas, and so forth, or indoors, such as in barns, garages, commercial buildings, homes, and so forth, or any area where pests are a problem, such as in shipping or storage containers (e.g., bags, boxes, crates, etc.), packing materials, bedding, and so forth; also includes the outer covering of a living being, such as skin, fur, hair, or clothing.

Isolongifolenone or at least one isolongifolenone analog and compositions containing isolongifolenone or at least one isolongifolenone analog can therefore be used for repelling harmful or troublesome arthropods such as blood-sucking/feeding and biting insects, ticks and mites.

The arthropods include mosquitoes (for example *Aedes, Culex* and *Anopheles* species), sand flies (for example *Phlebotomus* and *Litzomyia* species), bed bugs (for example *Cimex lectularius*), owl gnats (*Phlebotoma*), blackfly (*Culicoides* species), buffalo gnats (*Simulium* species), biting flies (for example *Stomoxys calcitrans*), tsetse flies (*Glossina* species), horseflies (*Tabanus, Haematopota* and *Chrysops* species), house flies (for example *Musca domestica* and *Fannia canicularis*), meat flies (for example *Sarcophaga carnaria*), flies which cause myiasis (for example *Lucilia cuprina, Chrysomyia chiloropyga, Hypoderma bovis, Hypoderma lineatum, Dermatobia hominis, Oestrus ovis, Gasterophilus intestinalis* and *Cochliomyia hominovorax*), bugs (for example *Cimex lectularius, Rhodnius prolixus* and *Triatoma infestans*), lice (for example *Pediculus humanus, Haematopinus suis* and *Damalina ovis*), louse flies (for example *Melaphagus orinus*), and fleas (for example *Pulex irritans, Cthenocephalides canis* and *Xenopsylla cheopis*) and sand fleas (for example *Dermatophilus penetrans*).

The harmful or troublesome insects include cockroaches (for example *Blattella germanica, Periplaneta americana, Blatta orientalis* and *Supella supellectilium*), beetles (for example *Sitophilus granarius, Tenebrio molitor, Dermesies lardarius, Stegobium paniceum, Anobium puntactum* and *Hylotrupes bajulus*), termites (for example *Reticulitermes lucifugus*) and ants (for example *Lasius niger*).

The blood-feeding ticks include, for example, *Ornithodorus moubata, Ixodes ricinus, Ixodes scapularis, Boophilus microplus, Amblyomma americanum,* and *Amblyomma hebreum.*, and mites include, for example, *Sarcoptes scabiei* and *Dermanyssus gallinae*.

The compounds according to the invention, which can be used in undiluted or diluted form, can be converted into formulations customary for repellents. It can be used in all the presentation forms customary in cosmetics, for example in the form of solutions, emulsions, gels, ointments, pastes, creams, powders, sticks, sprays or aerosols from spray cans.

For use in the non-cosmetic sector, the compounds can be incorporated, for example, into granules, oily spraying agents or slow release formulations.

The formulations are prepared in a known manner by mixing or diluting the compounds according to the invention with solvents (for example xylene, chlorobenzenes, paraffins, methanol, ethanol, isopropanol or water), carriers (for example kaolins, aluminas, talc, chalk, highly disperse silicic acid and silicates), emulsifying agents (for example polyoxyethylene fatty acid esters, polyoxyethylene fatty alcohol ethers, alkylsulphonates and arylsulphonates) and dispersing agents (for example lignin, sulphite waste liquors and methylcellulose).

The compounds according to the invention can be used as mixtures with other known active compounds (for example sunscreen agents). The formulations in general contain between about 0.1 and about 95% (e.g., 0.1-95%) by weight of active compound, preferably between about 0.5 and about 90% (e.g., 0.5-90%), more preferably between about 0.5 and about 40% (e.g., 0.5-40%).

For protection from arthropods such as blood-sucking insects or ticks or mites, the compounds according to the invention are generally either applied to human or animal skin, or items of clothing and other objects are treated with the compound.

The compounds according to the invention are also suitable as an additive to impregnating agents for, for example, textile webs, articles of clothing and packaging materials, and as an additive to polishing, cleaning and window-cleaning agents.

The compositions of the present invention contain a carrier and the compound. The repellent of the present invention is generally applied with-a carrier component. The carrier component can be a liquid or a solid material. As is known in the art, the vehicle or carrier to be used refers to a substrate such as a gel, polymers, or the like. All of these substrates have been used to release insect repellents and are well known in the art.

The amount of the compound used will be at least an effective amount. The term "effective amount," as used herein, means the minimum amount of the compound needed to reduce the number of arthropod (e.g., *Aedes aegypti*) bites on a treated area or object (e.g., mammalian skin which has been treated topically with the compound of the present invention) when compared to the same area or object which is untreated. The term "effective amount," as used herein, also means the minimum amount of the compound needed to cause arthropods to make oriented movements away from a treated area or object (e.g., mammalian skin which has been treated topically with the compound of the present invention) when compared to the same area or object which is untreated. For example, generally about 10-300 (e.g., 10-300) nmole isolongifolenone or isolongifolenone analog/cm$^2$ cloth or skin is used, preferably about 10-200 (e.g., 10-200) nmole/cm$^2$ cloth or skin, more preferably about 20-100 (e.g., 20-100) nmole/cm$^2$ cloth or skin, and most preferably about 20-80 (e.g., 20-80) nmole/cm$^2$ cloth or skin. Effective concentrations of the compound in the compositions generally may vary between about 0.1 and about 95% (e.g., 0.1-95%) by weight, preferably between about 0.5 and about 90% (e.g., 0.5-90%). Of course, the precise amount needed will vary in accordance with the particular repellent composition used; the type of area or object to be treated; the number of hours or days of repelling needed; and the environment in which the area or object is located. The precise amount of repellent can easily be determined by one skilled in the art given the teaching of this application. For example, one skilled in the art could follow the procedure utilized below.

The compounds may be used with other repellents or arthropod control agents (e.g., insecticides, chemosterilants or the like). When used, these agents should be used in an amount which, as readily determined by one skilled in the arts, will not interfere with the effectiveness of the compound.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Synthesis of isolongifolenone: Without being bound by theory, successful conversion of isolongifolene into isolongifolenone 1 depends on the selectivity of the allylic oxidation of alkene into an $\alpha,\beta$-unsaturated ketone without double bond migration or epoxidation. Our investigations involved the utilization of peroxides, such as hydrogen peroxide, tert-butyl hydroperoxide, and cumene hydroperoxide as the oxidants, with or without chromium hexacarbonyl as the catalyst. The same amount of isolongifolene was used as the starting material in the different reactions and the results are summarized in Table 1.

Without being bound by theory, apparently the production of isolongifolenone 1 was influenced by the oxidants and the catalyst used during certain oxidation processes. It was found that peracetic acid efficiently oxidized isolongifolene in less than 2 h, but the saturated ketone 4 was the main product whereas the isolongifolenone 1 was less than 1% (entries 4 and 5), and the reaction was not influenced by the catalyst. In the case of cumene hydroperoxide (entries 19-25), isolongifolenone 1 was the predominate product, however 11-24% of other isomers were formed. Hydrogen peroxide gave poor oxidation results, varying amounts of 1 to 5 and other identified compounds were produced (entries 1-3). During the course of these studies it was surprisingly observed that a high degree of allylic oxidation selectivity in the conversion of isolongifolene into isolongifolenone 1 was achieved using tert-butyl hydroperoxide as the oxidant and chromium hexacarbonyl as the catalyst with a surprisingly short-reaction time (entries 11-18). For example, the conversion rate surprisingly was about 99% and 90% isolongifolenone 1 was formed after 2 h oxidation. At 3.5 h, the isolongifolene surprisingly was oxidized 100% and 93% isolongifolenone 1 was achieved. However, the conversion rate was only about 38% and less than 80% isolongifolenone 1 was detected in the oxidation products without the chromium hexacarbonyl catalyst after 4 h oxidation (entry 7), indicating that the selectivity of allylic oxidation of isolongifolene was effectively influenced by this catalyst.

General synthesis of isolongifolenone: t-butyl hydroperoxide (0.61 mL, 4.40 mmol) was added dropwise to a solution of (−)-isolongifolene (300 mg, 1.47 mmol, purity 98% GC, b.p. 255-256° C.; Sigma, St. Louis, Mo.) and chromium hexacarbonyl (161 mg, 0.73 mmol) in 4 mL of acetonitrile and 0.4 mL of benzene (benzene promoted the dissolution of isolongifolene into acetonitrile). The resulting reaction mixture was boiled gently under reflux at ~82° C. for 4 hours and the reaction was tracked by GC. After the GC peak of starting material isolongifolene completely disappeared the reaction mixture was cooled to room temperature using an ice-bath, filtered through a sintered funnel, and the precipitate (chromium hexacarbonyl) was washed with cold benzene (3×4 mL). The filtrate was diluted with hexane and washed with water (3×5 mL), brine, and dried over $Na_2SO_4$. The solvent was evaporated under reduced pressure to give 315.6 mg of crude product (yield 98.4%, purity 93.9%). The isolongifolenone was purified by a flash chromatography on silica gel using hexane-ethyl acetate (5:1 v/v) as eluent to provide 264 mg (1.21 mmol, 82.4% yield, 99.7% purity) of isolongifolenone 1 as a colorless liquid. at room temperature.

mp: 31-32° C. $[\alpha]_D^{26}$ –153.30 (c 10.45, MeOH). $^1$H-NMR (CDCl$_3$, 400 MHz): δ 0.94 (3H, s, CH$_3$), 1.00 (3H, s, CH$_3$), 1.03 (3H, s, CH$_3$), 1.08 (3H, s, CH$_3$), 1.96-1.28 (1H, m), 1.35 (1H, d, J=10.2 Hz), 1.57 (1H, m), 1.62 (1H, dq, J=10.2, 2.0 Hz), 1.67-1.73 (1H, m), 1.87 (1H, dd, J=12.0, 4.0 Hz), 1.92 (1H, d, J=4.0 Hz), 2.00 (1H, d, J=16.0 Hz, O═CC—H), 2.33 (1H, d, J=16.0 Hz, O═CC—H), 5.65 (1H, s, ═C—H). $^{13}$C-NMR (CDCl$_3$, 100 Hz): δ 24.26, 24.50, 25.32, 25.69, 26.91, 27.76, 34.36, 36.62, 44.00, 46.43, 49.83, 58.54, 116.78, 183.82, 200.10. EI-MS m/z (%): 218 [M]$^+$ (56), 203 (13), 189 (8), 175 (100), 162 (73), 147 (58), 133 (23), 119 (25), 105 (21), 91 (29), 77 (12), 69 (9), 55 (8).

Mosquito Bioassay: Yellowfever mosquito, *Aedes aegypti* (red eye Liverpool strain) and malarial vector mosquito, *Anopheles stephensi* used in the study were from colonies maintained at the Walter Reed Army Institute of Research, Department of Entomology, Silver Spring, Md. The mosquitoes were reared using the procedure of Gerberg et al. (Gerberg, E. J., et al., Manual for mosquito rearing and experimental techniques, 1994, AMCA Inc., Lake Charles, La.). Larvae were fed ground tropical fish flakes (Tetramin Tropical Fish Flakes, Tetra Sales, Blacksburg, Va., www.tetra-fish.com). Colonies were maintained in a photoperiod of 12:12 h (L:D with lights on at 0600 h) at 27° C. and 80% RH. Adult mosquitoes were supplied with cotton pads moistened with 10% aqueous sucrose solution.

The comparative mosquito biting-deterrent activity of isolongifolenone and Deet was evaluated using the mosquitoes *A. degypti* and *An. stephensi*. Isolongifolenone was synthesized as described earlier. The well known and widely used synthetic repellent chemical Deet (McCabe, E. T., et al., J. Org. Chem., 19: 493-498 (1954)) was purchased from Morflex, Inc., Greensboro, N.C. Deet is often considered to be the best mosquito repellent ever developed (Elston, D. M., J. Am. Acad. Dermatol., 36: 644-645 (1998)) and is used as a gold standard to which new candidate repellents are compared. A comparative bioassay of the two compounds was conducted by using the in vitro K&D module bioassay system (Klun et al., 2005). The K&D in vitro assay system consists of three components: (1) A Plexiglas™ 29.7 cm×7.1 cm K&D module composed of six adjacent cells each designed to hold mosquitoes and each having a rectangular 3×4 cm floor hole that opened and closed by a sliding door. (2) A Plexiglas™ six-well 29.7 cm×7.1 cm water water-bath warmed (38° C.) reservoir with six 3×4 cm wells designed to match the sliding-door openings of the K&D module base and to contain 6 mL warmed human red blood cells. The wells were covered with a collagen membrane (the blood cell-membrane unit simulated a human host for mosquito feeding). (3) A 29.7×7.1 cm×0.4 cm Teflon® separator having six rectangular openings like the K&D module. In the study, test compounds in 95% ethanol solution were applied to 3×4 cm cloth areas marked with ink pen on a 29.7-cm×7.1 cm strip of organdy cloth. We routinely applied ethanol solutions (115 µL) 0.5 cm outside of the 3×4 marked cloth areas to ensure that mosquitoes were never exposed to any area of untreated cloth. The treated areas (25 nmol/cm$^2$ cloth) matched and covered the collagen membrane covered blood-cell wells of the blood cells reservoir; the 25 nmol compound/cm$^2$ dose was used because previous dose×response bioassays with Deet and other standard repellent compounds showed that at this dose, applied to human skin or cloth, caused ca. 80% suppression of mosquito biting compared to controls (Klun et al., 2005; Klun, J. A., et al., J. Med. Entomology, 40: 293-299 (2003)). The Teflon® separator was placed over the treated cloth. The function of the separator was to prevent direct contact of the K&D module with chemically treated cloth. A bioassay replicate consisted of three treatments: isolongifolenone, Deet, and 95% ethanol treated cloth as control. We used two replicates with treatments randomly positioned over the six-cells of a reservoir.

The mosquito bioassays were conducted With the in vitro K&D module systems positioned in a Purair ductless chemical fume hood (Air Science USA, LLC, Fort Myers, Fla.) from 1300-1600 h over days at 24°-26° C. and 24-51%, RH in ambient laboratory light. Mated nulliparous *A. aegypti* and *A. stephensi* (5-15 d old) were tested, and they had no water 24 h before testing. Mosquitoes were loaded into each of six adjacent K&D module cells and promptly after loading they were exposed to 2 replicates of the three treatments on the organdy cloth. Routinely, a six-celled K&D module containing five mosquitoes/cell was positioned on the Teflon® separator over air-dried cloth treatments covering the blood-membrane wells, and trap doors of the K&D modules were opened to expose-the treatments to the sets of mosquitoes. After a 3-minute exposure, the number of mosquitoes biting through cloth treatments in each cell was recorded and mosquitoes were prodded back into the cells.

In a dose-response assay, *A. aegypti* was tested against Deet and (−)-isolongifolenone at 0, 4, 9, 16, 25, and 36 nmole compound/cm$^2$ cloth. Two hundred mosquitoes were tested against each dose of each compound. As a mosquito quality-control procedure in both the fixed dose and the dose-response assays, we arbitrarily analyzed only data sets in which three or more females bit (0.4 proportion or less not biting) in the control cell. This approach helped to assure that chemicals were evaluated using data obtained with aggressively-feeding mosquitoes.

In replicated tests, each of the chemical treatments was tested against 200 *A. aegypti* and 200 *A. stephensi* females (40 replicates). Isolongifolenone analogs were bioassayed comparatively against Deet and a control using the same procedures describe above, but using *A. aegypti* with 100 mosquitoes exposed to each compound (20 replicates). The not biting data were converted to proportion then transformed by the standard variance stabilizing transformation for proportions (arcsin $\sqrt{p}$, where p is the original proportion) in order to fit the assumption of homogeneity of variances for analysis of variance (ANOVA). Not biting means were compared by one-way ANOVA followed by Ryan-Einot-Gabriel-Welsch range test (SPSS 10.0 for Windows for significance at $\alpha$=0.05 level, George, D., and P. Mallery, SPSS for Windows step by step: A simple guide and reference, 4th ed., 2002, Allyn & Bacon, Boston, Mass.).

Tick Bioassay: Blacklegged tick (*Ixodes scapularis*) nymphs were reared from larvae obtained from the laboratory colony at Oklahoma State University, Stillwater, Okla., and fed on rats (Beltsville Area Animal Care and Use Committee Protocol #05-0122) at the U.S. Department of Agriculture (USDA), Agricultural Research Service (ARS), Beltsville Agricultural Research Center, Beltsville, Md. Lone star tick (*Amblyomma americanum*) nymphs were obtained from a colony at the USDA, ARS, Knipling-Bushland U.S. Livestock Insects Research Laboratory, Kerrville, Tex. Both species of ticks were maintained at 24° C.; ~97% RH and 16:8 h LD until testing.

The fingertip bioassay used by Schreck et al. (Schreck, C. E., et al., J. Am. Mosq. Control Assoc., 11: 136-140 (1995)) was modified (Carroll, J. F., et al., Exp. Appl. Acarol., 41: 215-224 (2007); Carroll, J. F., et al., Med. Vet. Entomol., 19:101-106 (2005)) by applying treatments to the outer layer of a strip of cloth (organdy) later doubly wrapped around the middle phalanx of an index finger. A 7×7 mesh/nm strip of organdy cloth (G Street Fabrics, Rockville, Md.) was cut in the shape of a hockey stick (9 cm long section, 4.5 cm short section, 4-4.5 cm wide) so that when the cloth was wrapped twice around the middle phalanx of the index finger it completely covered the area between the deepest creases of the distal and middle joints of the finger of a volunteer subject. The cloth extended 5-6 mm proximally beyond the deepest crease of the middles joint and overlapped 1-3 mm. With the strip of cloth in place, the boundaries of the area to receive the repellent treatment area (between the deepest creases of the distal and middle joints) were marked on the cloth with a lead pencil. This cloth was used as a template for tracing the boundaries on other cloths.

Stoichiometrically equivalent stock 95% ethanol solutions of the compounds were prepared: 50 nmol Deet/µL and 50 nmol isolongifolenone or isolongifolenone analog/µL for use in all bioassays. The volumes of the respective solutions used to generate 155 nmole repellent doses/$cm^2$ cloth were based on the dimensions of the middle phalanx of the left index finger of a volunteer subject. The volume of the treated solutions required to give the desired nmoles/$cm^2$ cloth dosages was calculated from the average of the circumferences of the two finger joints multiplied by the distance between the deepest crease of each joint.

A repellent solution (52 µL) or ethanol (control) of the same volume was applied to the designated treatment area on the cloth and allowed to dry. As with Schreck et al. (1995), it was necessary to screen *I. scapularis* nymphs for active individuals. While the treated cloth dried, *I. scapularis* nymphs were transferred by forceps from a holding vial to a finger. Ten ticks that crawled ≧5 mm were sequestered in a Petri dish that had been glued inside a larger Petri dish with water added to the space between their sides to form a moat. After the cloth dried (10-12 min), it was wrapped twice around the index finger. To keep the cloth wrapped around the finger, three small dabs of beeswax were smeared on the upper surface of the inner layer of cloth at the edge of the overlap and pressure applied for 10 s. Using forceps, the 10 selected ticks were placed on the tip of the horizontally held finger between the nail and the edge of the cloth. When the tenth tick was placed on the finger, the finger was slowly tipped vertically with the tip downward. The locations of the ticks were recorded at 1, 3, 5, 10 and 15 min after their release on the finger. Host-seeking *A. americanum* are notably more active than *I. scapularis*, so 10 *A. americanum* nymphs were allowed to crawl directly from an open vial onto the fingertip. For both species, the finger was held over moated Petri dishes while ≧1 tick was on it. During bioassays temperatures ranged from 23°-26° C. and 10-56% RH. The repellent data were compared by paired samples t-test (SPSS 10.0 for Windows for significance at α=0.05 level, George, D., and P. Mallery, SPSS for Windows step by step: A simple guide and reference, 4th ed., 2002, Allyn & Bacon, Boston, Mass.).

One dose (155 nmole of compound/$cm^2$ cloth) of repellent and ethanol were tested against four groups of 10 *A. americanum* nymphs and four groups of *I. scapularis* nymphs. For dose response test, three doses (19.5, 39, and 78 nmole of compounds/$cm^2$ cloth) of each of Deet, isolongifolenone, and ethanol control (95%) were tested against four groups of 10 *I. scapularis* nymphs. Ticks were considered repelled if they had dropped from the finger or were on the untreated tip at 10 min after they were placed on the finger.

Figure 2:
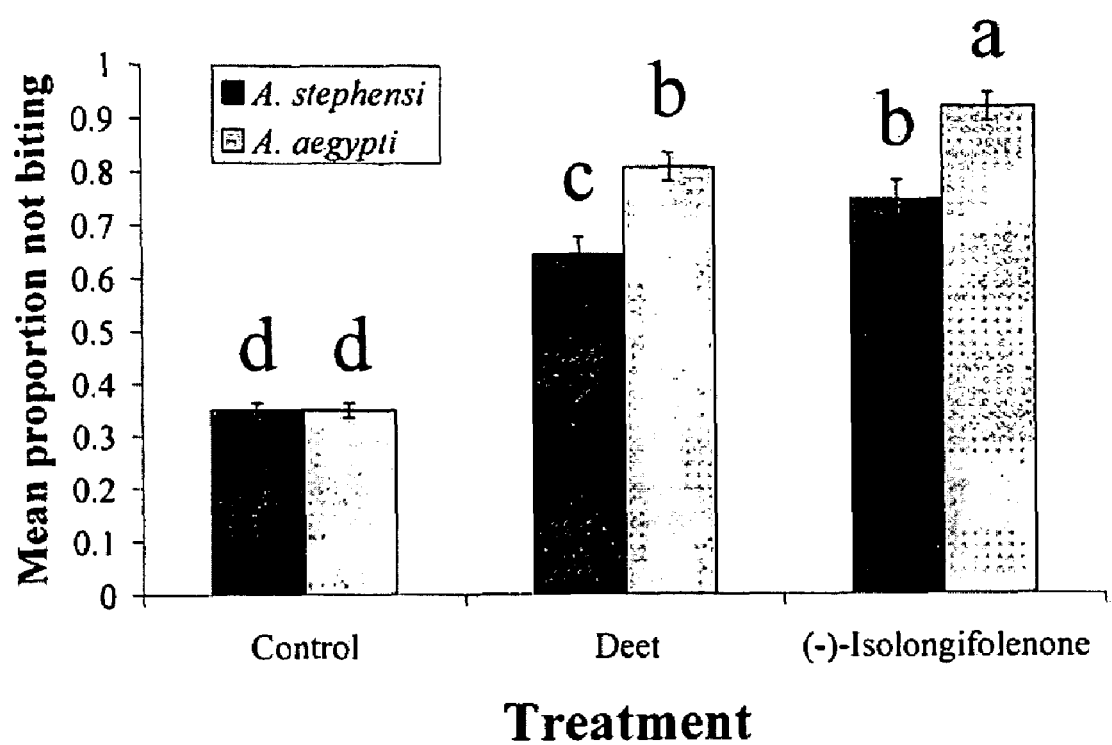
FIG. 2 shows the mean proportions of female *Aedes aegypti* and *Anopheles stephensi* not biting (±SE) exposed to isolongifolenone (25 nmole/cm$^2$ cloth) and Deet (25 nmole/cm$^2$ cloth) and a blank control (95% ethanol) in an in vitro K&D module (Klun & Debboun module bioassay system; Klun, J. A., et al., J. Amer. Mosquito Control Assoc., 21: 64-70 (2005)). Two hundred females of each mosquito species were tested against each treatment. Means followed by the different letters are significantly different at $\alpha=0.05$ [n=40, F(5,234)=67.03, P<0.0001)].
Figure 3:
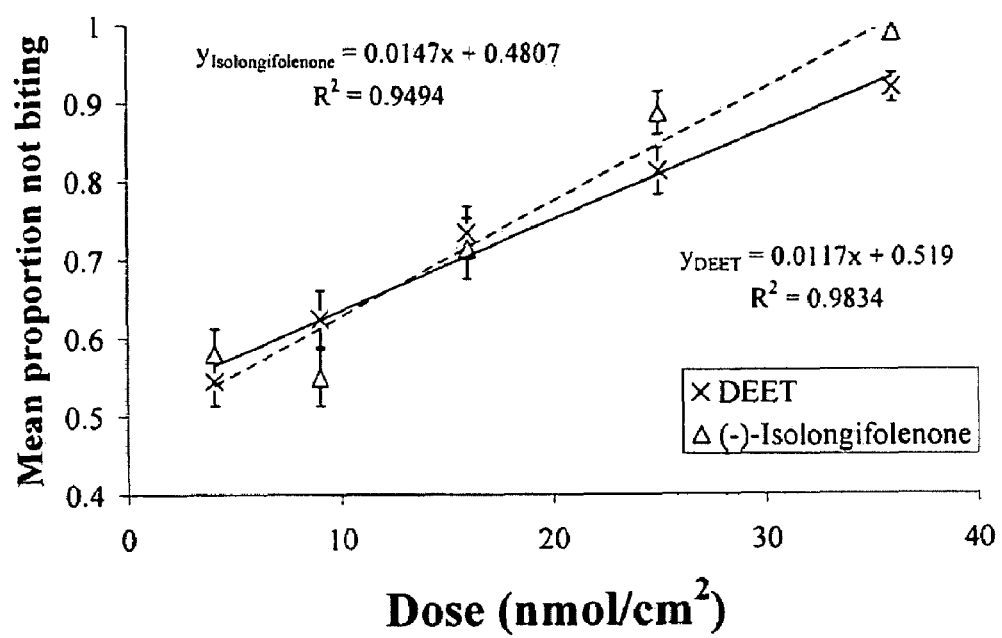
FIG. 3 shows dose-responses of female *A. aegypti* not biting in the in vitro K&D bioassay at five concentrations of DEET and isolongifolenone (4, 9, 16, 25, and 36 nmole compound/cm$^2$ cloth). Two hundred mosquitoes were tested against each dose of each compound. The proportions of mosquitoes deterred by (−)-isolongifolenone were significantly greater than the proportions deterred by DEET at doses of 25 and 36 nmole compound/cm$^2$ cloth, respectively (n=40, F(2, 117)=107.47, P<0.0001; n=40, F(2, 117)=329.38, P<0.0001).
Figure 6:
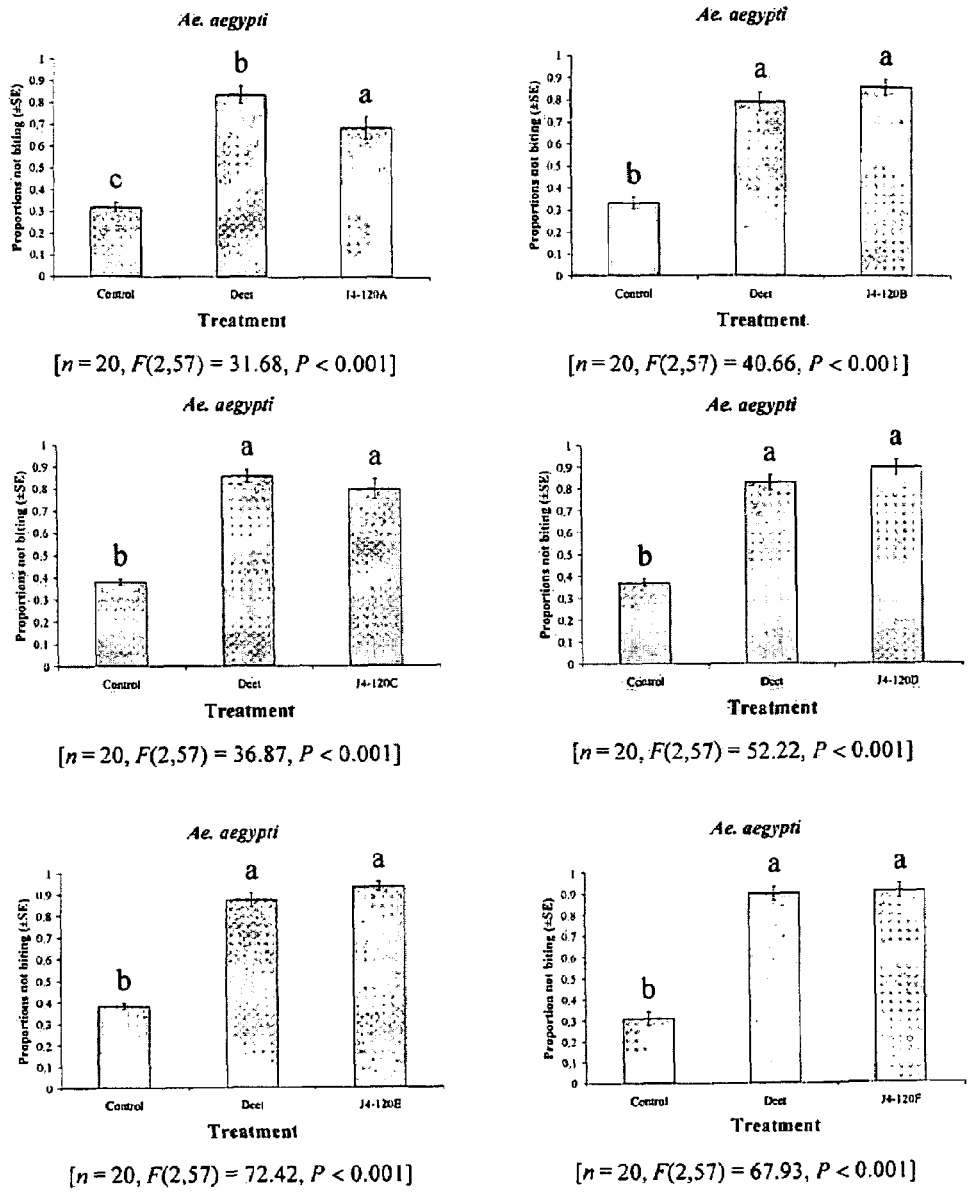
FIG. 6 shows the mean proportions of female *Ae. aegypti* not biting (±SE) when exposed to (−)-isolongifolenone analogs, Deet at 25 nmole/cm$^2$ cloth, and 95% ethanol control in the in vitro K&D bioassay. Means followed by the different letters are significantly different at $\alpha=0.05$.

Results and Discussion: FIG. 2 shows the repellency of 25 nmol/$cm^2$ cloth doses of isolongifolenone, Deet, and the control in bioassays with the mosquitoes *A. aegypti* and *A. Stephensi*. The proportions of mosquitoes that did not bite were significantly greater for isolongifolenone and Deet than for the control, and isolongifolenone surprisingly deterred the biting of *A. aegypti* and *A. stephensi* more effectively than Deet. The biting deterrent activity of (−)-isolongifolenone and Deet against *A. aegypti* increased over increasing concentrations. Regression analysis of the data for the proportion of not biting showed the dose-response relationship was linear (FIG. 3). Surprisingly the proportions of mosquitoes deterred by (−)-isolongifolenone were significantly greater than the proportions deterred by Deet at doses of 25 and 36 nmole compound/$cm^2$ cloth, respectively. FIG. 6 shows the repellency of 25 nmol/$cm^2$ cloth doses of isolongifolenone analogs, Deet, and the control in bioassays with the mosquitoes *A. aegypti*. The proportions of mosquitoes that did not bite were significantly greater for isolongifolenone analogs and Deet than for the control (surprisingly the isolongifolenone analogs were generally as effective as Deet), but isolongifolenone-analogs did not deter-the biting of *A. aegypti* more effectively than Deet which is contrary with isolongifolenone (FIG. 2).

Table 2 shows the results of tick bioassays using 155 nmol/$cm^2$ cloth dose of isolongifolenone and compared to control against *I. scapularis* and *A. americanum*. Surprisingly, the proportion of ticks repelled by isolongifolenone was significantly higher than for the control. Thus, isolongifolenone is a new lead compound that represents an alternative to traditional synthetic compounds that have been developed and used for protection against blood-feeding arthropods that vector human disease.

Figure 4:
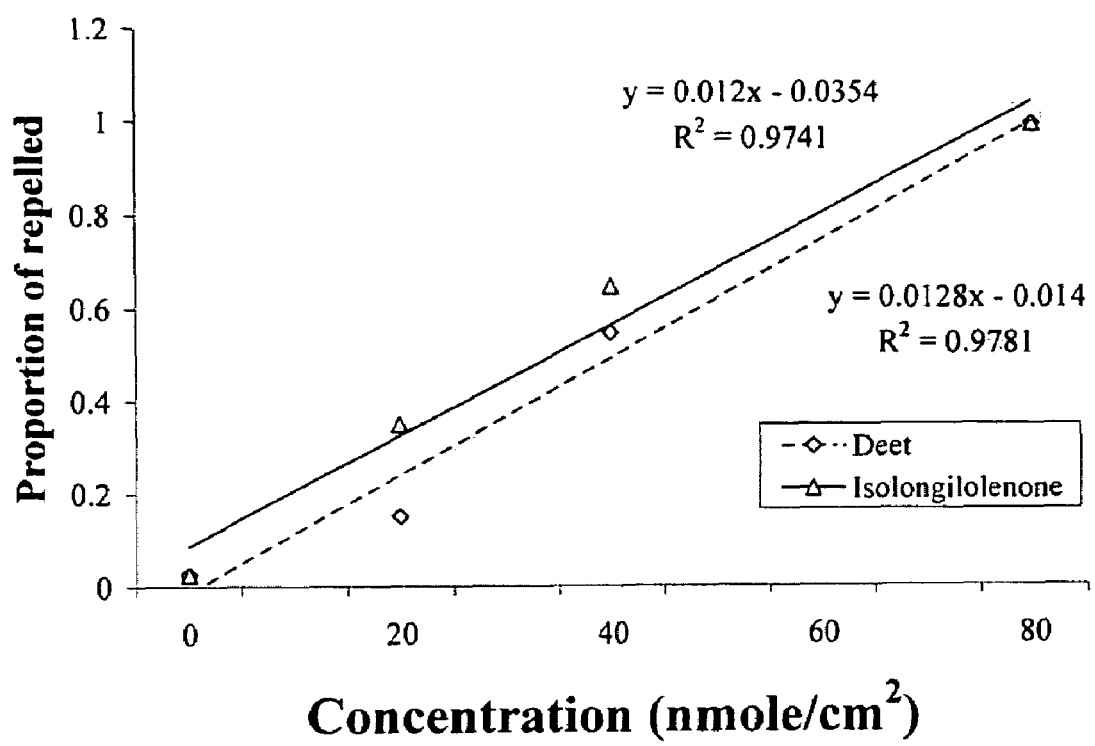
FIG. 4 shows the dose responses of *Ixodes scapularis* nymphs in fingertip bioassays (treated-cloth strip wrapped around finger) to three concentrations of Deet and isolongifolenone (19.5, 39, and 78 nmole of compounds/cm$^2$-cloth) and ethanol (95%) as a blank control (compound concentration of zero). The total number of *I. scapularis* nymphs tested for each treatment was 40.

Our experimental data indicated that the increasing proportion of *I. scapularis* nymphs repelled by isolongifolenone and Deet over increasing concentrations (19.5, 39, and 78 nmole of compounds/$cm^2$ cloth) followed first order kinetics. Dose response curves were best described by-equations: $Y=0.012x-0.0354$, $r^2=0.9741$ for isolongifolenone and $Y=0.0128x-0.014$, $r^2=0.9781$ for Deet, respectively. At 78 nmole/$cm^2$ cloth, surprisingly both isolongifolenone and Deet repelled 100% of the *I. scapularis* nymphs (FIG. 4). However, at 39 nmole/$cm^2$ cloth, isolongifolenone and Deet repelled 65% and 55% of the *I. scapularis* nymphs, respectively, and at 19.5 nmole/$cm^2$ cloth isolongifolenone and Deet repelled 35% and 15%, respectively.

Figure 7:
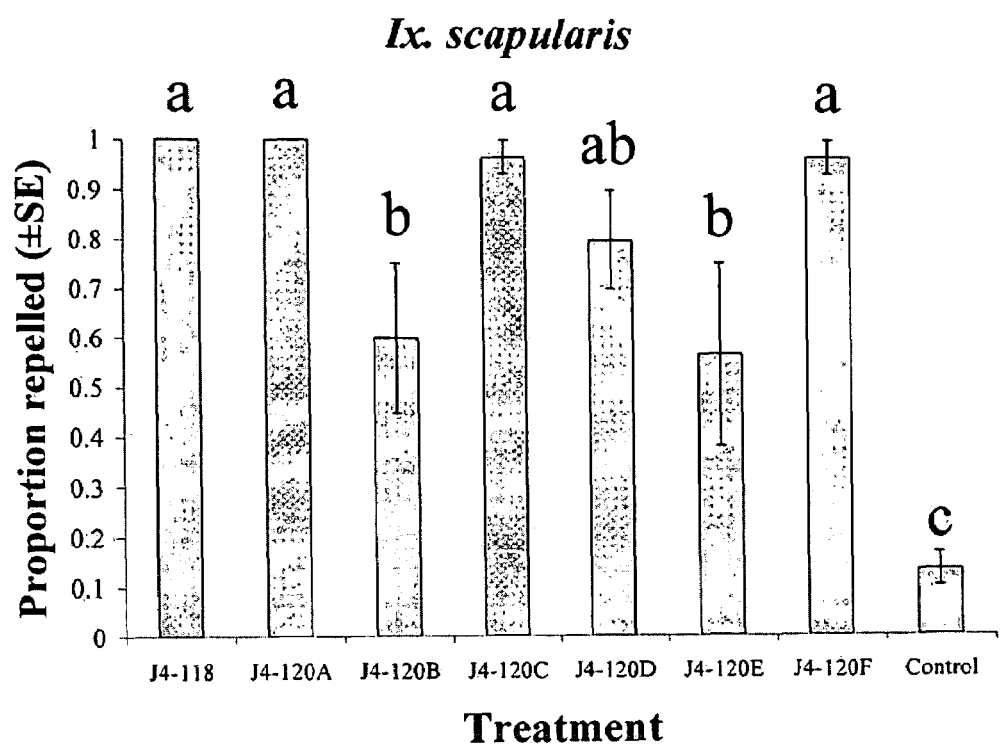
FIG. 7 shows mean proportions of *Ix. scapularis* tick nymphs repelled by (−)-isolongifolenone (J4-118) and analogs of isolongifolenone at 155 nmole/cm$^2$ cloth, and 95% ethanol control in finger tip bioassay. Ticks that were on untreated fingertip or had fallen off the finger at 15 min after they were released on the finger were considered repelled. Means followed by the different letters are significantly different at $\alpha=0.05$ [n=3, F(7, 16)=13.66, P<0.0001].

FIG. 7 shows the results of tick bioassays using 155 nmol/$cm^2$ cloth doses of isolongifolenone analogs compared to isolongifolenone and control against *I. scapularis*. Surprisingly the proportion of ticks repelled by all isolongifolenone analogs were significantly higher than for the control and some isolongifolenone analogs were as effective as isolongifolenone.

Our data thus showed the repellent effects of isolongifolenone and isolongifolenone analogs against blood-feeding arthropods. Bioassays showed that isolongifolenone deterred the biting of two species of mosquitoes, *A. aegypti* and, *A. stephensi*, more effectively than Deet, a benchmark repellent used worldwide, and most isolongifolenone analogs deterred the biting of *A. aegypti* as effectively as Deet. We also found that isolongifolenone and some isolongifolenone analogs repelled the tick, *I. scapularis*, as effectively as Deet. However, at lower concentration the isolongifolenone showed higher effectiveness against *I. scapularis* compared to Deet.

All of the references cited herein, including U.S. Patents, are incorporated by reference in their entirety. Also incorporated by reference in their entirety are the following references: Muthyala, R. S., et al., J. Med. Chem., 46: 1589-1602 (2003); Novak, R. J., and E. J. Gerberg, J. Am. Mosquito Control Assoc. (Supplement), 21: 7-11 (2005); Shiino, M., et al., Bioorg. Med. Chem., 9: 1233-1240 (2001).

Thus, in view of the above, the present invention concerns (in part) the following:

A method for making isolongifolenone, comprising (or consisting essentially of or consisting of) reacting (−)-isolongifolene with chromium hexacarbonyl and t-butyl hydroperoxide to make (−)-isolongifolenone. The above method, wherein said method comprises (or consists essentially of or consists of) reacting (−)-isolongifolene with chromium hexacarbonyl and t-butyl hydroperoxide in a solution containing acetonitrile and benzene. The above method, wherein said solution contains about 1 molar isolongifolene, about 0.3-about 1 molar equivalents of chromium hexacarbonyl, and about 2-about 5 molar equivalents of t-butyl hydroperoxide, and about 80-about 95% (w/w) acetonitrile and about 8-about 9.5% (w/w) benzene based on isolongifolene. The above method, wherein said reacting is at a temperature of about 80° to about 82° C. The above method, wherein said reacting is for about 2 to about 4 hours. The above method, wherein the conversion rate was about 99% and about 90% isolongifolenone was formed after a reaction time of about 2 hours. The above method, wherein the conversion rate was about 100% and about 93% isolongifolenone was formed after a reaction time of about 3.5 hours. The above method, wherein the purity of the isolongifolenone is about 94%. The above method, further comprising purifying said isolongifolenone to more than about 99% purity.

A method for repelling arthropods, comprising (or consisting essentially of or consisting of) treating an object or area with an arthropod repelling effective amount of isolongifolenone or isolongifolenone analog and optionally a carrier or carrier material. Preferably a carrier or carrier material is used. The above method, wherein said arthropod repelling effective amount of isolongifolenone or isolongifolenone analog is about 10-about 300 nmole isolongifolenone or isolongifolenone analog/cm² or is; about 10-about 200 nmole isolongifolenone or isolongifolenone analog/cm² or is about 20-about 100 nmole isolongifolenone or isolongifolenone analog/cm² or is about 20-about 80 nmole isolongifolenone or isolongifolenone analog/cm². The above method, wherein said arthropods are selected from the group consisting of *Aedes* species, *Culex* species, *Anopheles* species, *Ornithodorus* species, *Ixodes* species, *Boophilus* species, *Amblyomina* species, and mixtures thereof. The above method, wherein said arthropods are selected from the group consisting of *Aedes aegypti, Anopheles stephensi, Ixodes scapularis, Amblyomma americanum*, and mixtures thereof. The above method, wherein said arthropods are selected from the group consisting of *Aedes aegypti, Anopheles stephensi*, and mixtures thereof. The above method, wherein said arthropods are selected from the group consisting of *Ixodes scapularis, Amblyomma americanum*, and mixtures thereof.

A method for repelling arthropods, said method comprising treating an object or area with an arthropod repelling effective amount of at least one isolongifolenone analog and optionally a carrier or carrier material; wherein said at least one isolongifolenone analog has the following formula:

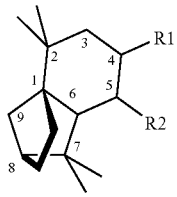

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen.

The above method, wherein said $R_1$ or $R_2$ is methanol, ethanol, ethanal, 4-methylhexane, or heptyloxymethane or wherein said $R_1$ and $R_2$ are methanol, ethanol, ethanal, 4-methylhexane, or heptyloxymethane.

The above method, wherein said acid is formic acid, acetic acid, 2-methylbutyric acid, or 3-methyl-2-butenoic acid.

The above method, wherein said $R_1$ or $R_2$ is hydrogen or said $R_1$ and $R_2$ are hydrogen.

The above method, wherein said $R_1$ or $R^2$ are hydrogen but said $R^1$ and $R^2$ are not both hydrogen.

The above method, wherein there is a double bond between carbons 5 and 6 and $R_2$ is hydrogen.

The above method, wherein said at least one isolongifolenone analog is selected from the group consisting of a (1R,8S)-2,2,7,7-tetramethyltricyclo[6.2.1.0$^{1,6}$]undec-5-ene having the formula:

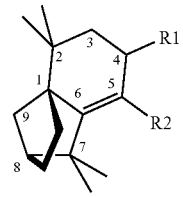

wherein $R^1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen;

a (1S,8S)-2,2,7,7-tetramethyltricyclo[6.2.1.0$^{1,6}$]undecane having the formula:

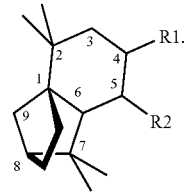

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen;

a tricyclo(1S,8S)-2,2,7,7-tetramethyltricyclo[6.2.1.0$^{1,6}$] undecane having the formula:

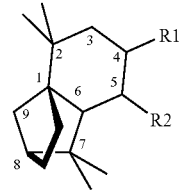

wherein $R_2$ is an oxygen, a $C_{1-10}$ alcohol, aldehyde, alkyl, ether, or esters of said alcohol with a $C_{1-10}$ saturated or unsaturated, straight or branched acid and $R_1$ is hydrogen;

The above method, wherein said at least one isolongifolenone analog is selected from the group consisting of

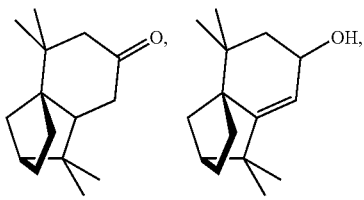

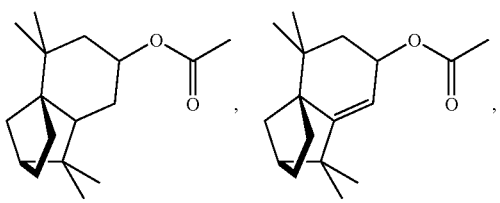

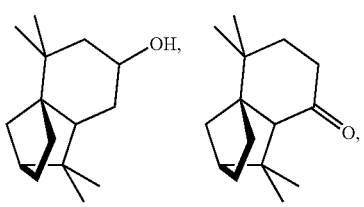

and mixtures thereof.

The above method, wherein said at least one isolongifolenone analog is

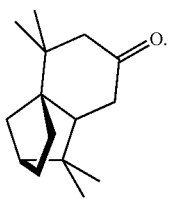

The above method, wherein said at least one isolongifolenone analog is

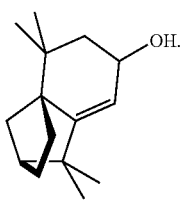

The above method, wherein said at least one isolongifolenone analog is

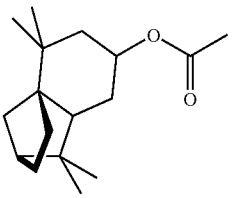

The above method, wherein said at least one isolongifolenone analog is

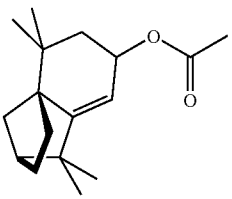

The above method, wherein said at least one isolongifolenone analog is

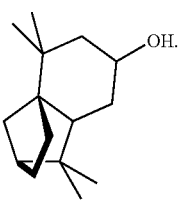

The above method, wherein said at least one isolongifolenone analog is

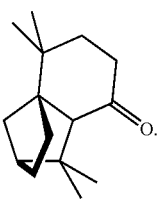

The above method, wherein said arthropod repelling effective amount of at least one isolongifolenone analog is about 10-about 300 nmole isolongifolenone analog/cm$^2$ or is about 10-about 200 nmole isolongifolenone analog/cm$^2$ or is about 20-about 100 nmole isolongifolenone analog/cm$^2$ or is about 20-about 80 nmole isolongifolenone analog/cm$^2$. The above method, wherein said arthropods are selected from the group consisting of *Aedes* species, *Culex* species, *Anopheles* species, *Ornithodorus* species, *Ixodes* species, *Boophilus* species, *Amblyomma* species, and mixtures thereof. The above method, wherein said arthropods are selected from the group consisting of *Aedes aegypti, Anopheles stephensi, Ixodes scapularis, Amblyomma americanum,* and mixtures thereof. The above method, wherein said arthropods are selected from the group consisting of *Aedes aegypti, Anopheles stephensi,* and mixtures thereof. The above method, wherein said arthropods are selected from the group consisting of *Ixodes scapularis, Amblyomma americanum,* and mixtures thereof.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Oxidation of isolongifolene under different conditions[a]

| Entry | Oxidants | Catalyst | Time (h) | Conversion (%) | \multicolumn{5}{c}{Product ratios (%)[b, c]} | Others[d] |
|---|---|---|---|---|---|---|---|---|---|---|
| | | | | | (2) | (3) | (4) | (5) | (1) | |
| 1 | $H_2O_2$ | $Cr(CO)_6$ | 1.0 | 18.7 | 23.5 | 11.5 | 16.4 | 7.7 | 35.3 | 5.6 |
| 2 | $H_2O_2$ | $Cr(CO)_6$ | 2.5 | 19.1 | 22.9 | 11.1 | 16.2 | 7.6 | 36.4 | 5.8 |
| 3 | $H_2O_2$ | $Cr(CO)_6$ | 18.0 | 46.6 | 14.4 | 6.2 | 23.4 | 7.4 | 37.7 | 10.9 |
| 4 | $CH_3COOOH$ | — | 1.8 | 99.8 | 0 | 0 | 83.9 | 3.1 | 0.8 | 12.2 |
| 5 | $CH_3COOOH$ | $Cr(CO)_6$ | 1.5 | 100 | 0 | 0 | 80.2 | 4.6 | 0.5 | 14.7 |
| 6 | $(CH_3)_3COOH$ | — | 1.0 | 17.9 | 2.5 | 2.4 | 7.3 | 7.8 | 75.4 | 4.6 |
| 7 | $(CH_3)_3COOH$ | — | 4.0 | 37.5 | 1.7 | 1.3 | 6.4 | 6.1 | 79.8 | 4.7 |
| 8 | $(CH_3)_3COOH$ | — | 16.0 | 70.8 | 0.9 | 0.8 | 2.9 | 4.0 | 84.7 | 6.7 |
| 9 | $(CH_3)_3COOH$ | — | 21.0 | 84.8 | 0.7 | 0.6 | 3.2 | 4.0 | 84.7 | 6.8 |
| 10 | $(CH_3)_3COOH$ | — | 23.5 | 95.1 | 0.1 | 0.1 | 2.4 | 3.0 | 77.1 | 17.3 |
| 11 | $CH_3COOOH$ | $Cr(CO)_6$ | 0.5 | 35.2 | 1.1 | 0.9 | 1.1 | 5.1 | 66.2 | 25.6 |
| 12 | $CH_3COOOH$ | $Cr(CO)_6$ | 1.0 | 88.7 | 1.5 | 0.7 | 1.1 | 2.7 | 85.0 | 9.0 |
| 13 | $CH_3COOOH$ | $Cr(CO)_6$ | 1.5 | 97.0 | 1.3 | 0.6 | 1.0 | 2.4 | 88.6 | 6.1 |
| 14 | $CH_3COOOH$ | $Cr(CO)_6$ | 2.0 | 98.9 | 1.3 | 0.6 | 1.2 | 2.1 | 90.7 | 4.1 |
| 15 | $CH_3COOOH$ | $Cr(CO)_6$ | 2.5 | 99.5 | 1.4 | 0.7 | 2.2 | 1.2 | 91.5 | 3.0 |
| 16 | $CH_3COOOH$ | $Cr(CO)_6$ | 3.0 | 99.6 | 1.5 | 0.8 | 1.5 | 1.9 | 91.7 | 2.6 |
| 17 | $CH_3COOOH$ | $Cr(CO)_6$ | 3.5 | 100 | 1.4 | 0.8 | 2.1 | 1.1 | 9.30 | 1.2 |
| 18 | $CH_3COOOH$ | $Cr(CO)_6$ | 4.0 | 100 | 1.5 | 1.0 | 2.3 | — | 93.2 | 2.0 |
| 19 | $C_6H_5C(CH_3)_2OOH$ | — | 2.0 | 59.2 | — | — | 10.5 | 5.9 | 76.6 | 6.9 |
| 20 | $C_6H_5C(CH_3)_2OOH$ | — | 4.5 | 73.4 | 1.0 | 1.1 | 7.8 | 6.3 | 76.6 | 7.2 |
| 21 | $C_6H_5C(CH_3)_2OOH$ | — | 70.0 | 76.6 | 1.3 | 1.3 | 4.7 | 6.6 | 81.5 | 4.6 |
| 22 | $C_6H_5C(CH_3)_2OOH$ | $Cr(CO)_6$ | 1.0 | 65.3 | — | — | 2.0 | 4.9 | 88.9 | 4.2 |
| 23 | $C_6H_5C(CH_3)_2OOH$ | $Cr(CO)_6$ | 4.0 | 80.6 | 1.1 | 0.8 | 1.4 | 4.4 | 88.0 | 4.3 |
| 24 | $C_6H_5C(CH_3)_2OOH$ | $Cr(CO)_6$ | 21.0 | 86.3 | 1.3 | 1.0 | 0.6 | 5.6 | 88.3 | 3.2 |
| 25 | $C_6H_5C(CH_3)_2OOH$ | $Cr(CO)_6$ | 45.0 | 86.7 | 1.2 | 1.0 | 1.0 | 5.4 | 88.5 | 2.9 |

[a]All chemicals were used in the same ratio.
[b]Determined by GC and GC-MS.
[c]

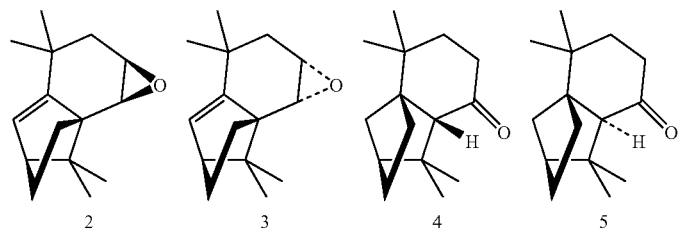

[d]Consisted of several unidentified components.

TABLE 2

Proportion of tick nymphs repelled by isolongifolenone in fingertip bioassays (155 nmol/cm² cloth). Ticks that were on untreated fingertip or had fallen off the finger at 10 min after they were released on the finger were considered repelled.*

| Species | Treatment | Proportion Repelled | t | P |
|---|---|---|---|---|
| *I. scapularis* | Control | 0.06 | | |
| | Isolongifolenone | 1.0 | −28.0 | <0.001 |
| *A. americanum* | Control | 0 | | |
| | Isolongifolenone | 0.725 | −7.03 | 0.006 |

*Three groups of 10 tick nymphs of *I. scapularis* and four groups of *A. americanum* were tested with isolongifolenone and control.

We claim:

1. A method for repelling arthropods, said method comprising treating an object or area with an arthropod repelling effective amount of at least one isolongifolenone analog and optionally a carrier or carrier material; wherein said at least one isolongifolenone analog has the following formula:

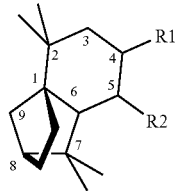

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen.

2. The method according to claim 1, wherein said $R_1$ or $R_2$ is methanol, ethanol, ethanal, 4-methylhexane, or heptyloxymethane or wherein said $R_1$ and $R_2$ are methanol, ethanol, ethanal, 4-methylhexane, or heptyloxymethane.

3. The method according to claim 1, wherein said acid is formic acid, acetic acid, 2-methylbutyric acid, or 3-methyl-2-butenoic acid.

4. The method according to claim 1, wherein said $R_1$ or $R_2$ is hydrogen or said $R_1$ and $R_2$ are hydrogen.

5. The method according to claim 1, wherein said $R^1$ or $R^2$ are hydrogen but said $R^1$ and $R^2$ are not both hydrogen.

6. The method according to claim 1, wherein there is a double bond between carbons 5 and 6 and $R_2$ is hydrogen.

7. The method according to claim 1, wherein said at least one isolongifolenone analog is selected from the group consisting of
   a (1R,8S)-2,2,7,7-tetramethyltricyclo[6.2.1.0$^{1,6}$]undec-5-ene having the formula:

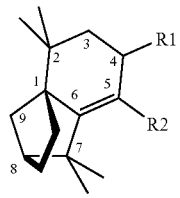

wherein $R^1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen;
   a (1S,8S)-2,2,7,7-tetramethyltricyclo[6.2.1.0$^{1,6}$]undecane having the formula:

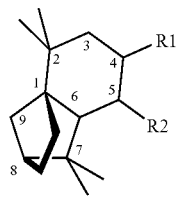

wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen;
   a tricyclo(1S,8S)-2,2,7,7-tetramethyltricyclo[6.2.1.0$^{1,6}$]undecane having the formula:

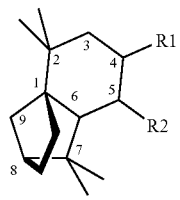

wherein $R_2$ is an oxygen, a $C_{1-10}$ alcohol, aldehyde, alkyl, ether, or esters of said alcohol with a $C_{1-10}$ saturated or unsaturated, straight or branched acid and $R_1$ is hydrogen.

8. The method according to claim 1, wherein said at least one isolongifolenone analog is selected from the group consisting of

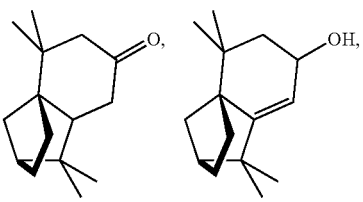

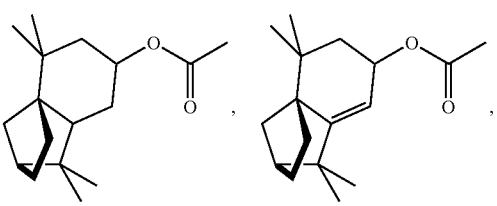

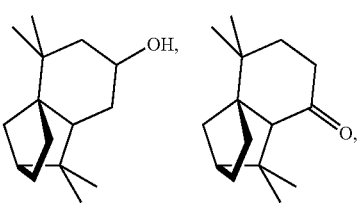

and mixtures thereof.

9. The method according to claim 1, wherein said at least one isolongifolenone analog is

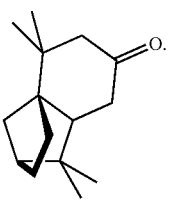

10. The method according to claim 1, wherein said at least one isolongifolenone analog is

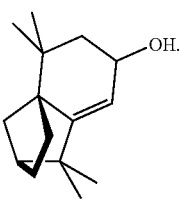

11. The method according to claim 1, wherein said at least one isolongifolenone alog is

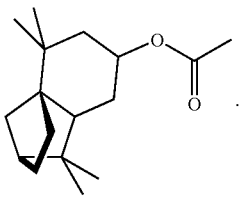

12. The method according to claim 1, wherein said at least one isolongifolenone analog is

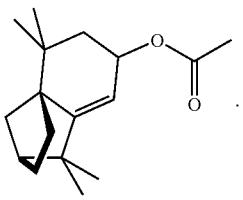

13. The method according to claim 1, wherein said at least one isolongifolenone analog is

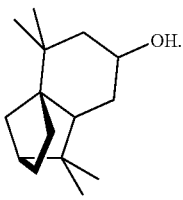

14. The method according to claim 1, wherein said at least one isolongifolenone analog is

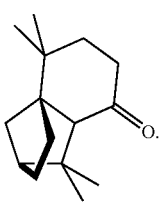

15. The method according to claim 1, wherein said arthropod repelling effective amount of at least one isolongifolenone analog is about 10-about 300 nmole/cm$^2$.

16. The method according to claim 1, wherein said arthropod repelling effective amount of at least one isolongifolenone analog is about 10-about 200 nmole/cm$^2$.

17. The method according to claim 1, wherein said arthropod repelling effective amount of at least one isolongifolenone analog is about 20-about 100 nmole/cm$^2$.

18. The method according to claim 1, wherein said arthropod repelling effective amount of at least one isolongifolenone analog is about 20-about 80 nmole isolongifolenone/cm$^2$.

19. The method according to claim 1, wherein said arthropods are selected from the group consisting of *Aedes* species, *Culex* species, *Anopheles* species, *Ornithodorus* species, *Ixodes* species, *Boophilus* species, *Amblyomma* species, and mixtures thereof.

20. The method according to claim 1, wherein said arthropods are selected from the group consisting of *Aedes aegypti, Anopheles stephensi, Ixodes scapularis, Amblyomma americanum,* and mixtures thereof.

21. The method according to claim 1, wherein said arthropods are selected from the group consisting of *Aedes aegypti, Anopheles stephensi,* and mixtures thereof.

22. The method according to claim 1, wherein said arthropods are selected from the group consisting of *Ixodes scapularis, Amblyomma americanum,* and mixtures thereof.

23. The method according to claim 1, wherein said arthropods are *Aedes aegypti.*

24. The method according to claim 1, wherein said arthropods are *Anopheles stephensi.*

25. The method according to claim 1, wherein said arthropods are *Ixodes scapularis.*

26. The method according to claim 1, wherein said arthropods are *Amblyomma americanum.*

* * * * *

(12) INTER PARTES REVIEW CERTIFICATE (42nd)
United States Patent　(10) Number:　　US 7,579,016 K1
Zhang et al.　　　　　　　(45) Certificate Issued:　Nov. 24, 2014

(54) METHODS FOR REPELLING ARTHROPODS USING ISOLONGIFOLENONE ANALOGS

(75) Inventors: Aijun Zhang; John F. Carroll; Shifa Wang; Jerome A. Klun

(73) Assignee: The United States of America, as Represented by the Secretary of Agriculture

Trial Number:

IPR2013-00124 filed Jan. 25, 2013

Petitioner: International Flavors & Fragrances, Inc.

Patent Owner: The United States of America, as Represented by the Secretary of Agriculture

Inter Partes Review Certificate for:

Patent No.: 7,579,016
Issued: Aug. 25, 2009
Appl. No.: 12/106,505
Filed: Apr. 21, 2008

The results of IPR2013-00124 are reflected in this inter partes review certificate under 35 U.S.C. 318(b).

INTER PARTES REVIEW CERTIFICATE
U.S. Patent 7,579,016 K1
Trial No. IPR2013-00124
Certificate Issued Nov. 24, 2014

AS A RESULT OF THE INTER PARTES REVIEW PROCEEDING, IT HAS BEEN DETERMINED THAT:

Claims 1-26 are cancelled.

27. (substitute for claim 1) *A method for repelling arthropods, said method comprising treating an object or area with an arthropod repelling effective amount of at least one isolongifolenone analog and optionally a carrier or carrier material; wherein said at least one isolongifolenone analog has the following formula:*

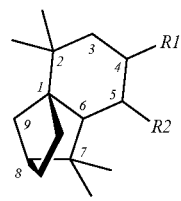

*wherein $R_1$ is hydrogen, an oxygen, a $C_{1-10}$ alcohol, aldehyde, alkyl, ether, or esters of said alcohol with a $C_{1-10}$ saturated or unsaturated, straight or branched acid and $R_2$ is hydrogen, an oxygen, a $C_{1-10}$ alcohol, aldehyde, alkyl, ether, or esters of said alcohol with a $C_{1-10}$ saturated or unsaturated, straight or branched acid; optionally there is a double bond between carbons 5 and 6 and $R_2$ is hydrogen;*
*wherein said at least one isolongifolenone analog is selected from the group consisting of*

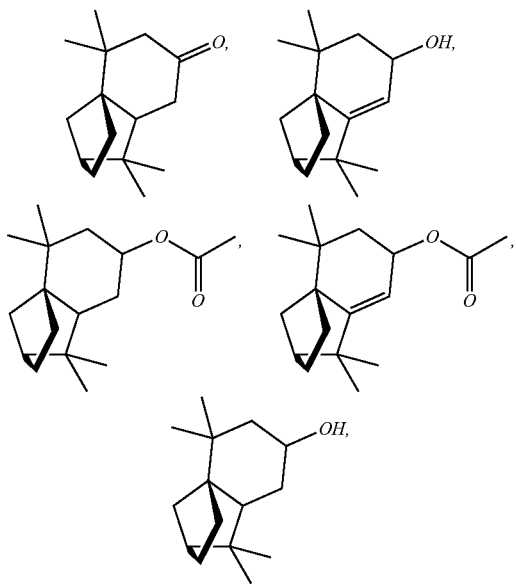

*and mixtures thereof.*

28. (substitute for claim 9) *The method according to claim 27, wherein said at least one isolongifolenone analog is*

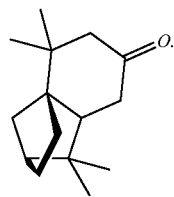

29. (substitute for claim 10) *The method according to claim 27, wherein said at least one isolongifolenone analog is*

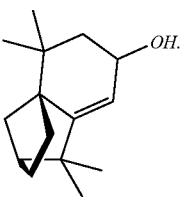

30. (substitute for claim 11) *The method according to claim 27, wherein said at least one isolongifolenone analog is*

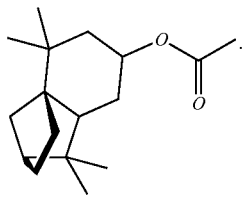

31. (substitute for claim 12) *The method according to claim 27, wherein said at least one isolongifolenone analog is*

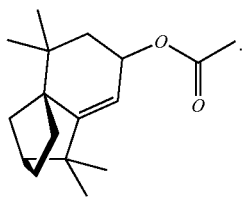

32. (substitute for claim 13) *The method according to claim 27, wherein said at least one isolongifolenone analog is*

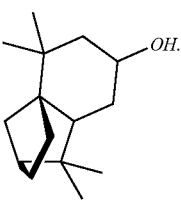

33. (substitute for claim 14) *The method according to claim 27, wherein said arthropod repelling effective amount of at least one isolongifolenone analog is about 10-about 300 $nmole/cm^2$.*

INTER PARTES REVIEW CERTIFICATE
U.S. Patent 7,579,016 K1
Trial No. IPR2013-00124
Certificate Issued Nov. 24, 2014

34. (substitute for claim 15) The method according to claim 27, wherein said arthropod repelling effective amount of at least one isolongifolenone analog is about 10-about 200 nmole/cm$^2$.

35. (substitute for claim 16) The method according to claim 27, wherein said arthropod repelling effective amount of at least one isolongifolenone analog is about 20-about 100 nmole/cm$^2$.

36. (substitute for claim 17) The method according to claim 27, wherein said arthropod repelling effective amount of at least one isolongifolenone analog is about 20-about 80 nmole isolongifolenone/cm$^2$.

37. (substitute for claim 18) The method according to claim 27, wherein said arthropods are selected from the group consisting of Aedes species, Culex species, Anopheles species, Ornithodorus species, Ixodes species, Boophilus species, Amblyomma species, and mixtures thereof.

38. (substitute for claim 19) The method according to claim 27, wherein said arthropods are selected from the group consisting of Aedes aegypti, Anopheles stephensi, Ixodes scapularis, Amblyomma americanum, and mixtures thereof.

39. (substitute for claim 20) The method according to claim 27, wherein said arthropods are selected from the group consisting of Aedes aegypti, Anopheles stephensi, and mixtures thereof.

40. (substitute for claim 21) The method according to claim 27, wherein said arthropods are selected from the group consisting of Ixodes scapularis, Amblyomma americanum, and mixtures thereof.

41. (substitute for claim 22) The method according to claim 27, wherein said arthropods are Aedes aegypti.

42. (substitute for claim 23) The method according to claim 27, wherein said arthropods are Anopheles stephensi.

43. (substitute for claim 24) The method according to claim 27, wherein said arthropods are Ixodes scapularis.

44. (substitute for claim 25) The method according to claim 27, wherein said arthropods are Amblyomma americanum.

\* \* \* \* \*